United States Patent

Mikus et al.

[11] Patent Number: 6,093,194
[45] Date of Patent: Jul. 25, 2000

[54] INSERTION DEVICE FOR STENTS AND METHODS FOR USE

[75] Inventors: Paul W. Mikus; Jay J. Eum, both of Aliso Viejo; Dennis Bui, Orange; Gregory Kelly, Mission Viejo, all of Calif.

[73] Assignee: Endocare, Inc., Irvine, Calif.

[21] Appl. No.: 09/152,557

[22] Filed: Sep. 14, 1998

[51] Int. Cl.⁷ ................................................. A61F 11/00
[52] U.S. Cl. ......................................... 606/108; 623/1.11
[58] Field of Search .................... 623/1, 2, 11; 606/194, 606/191, 198, 108, 192; 604/164

[56] References Cited

U.S. PATENT DOCUMENTS

| | | | |
|---|---|---|---|
| 3,868,956 | 3/1975 | Alfidi et al. | 128/345 |
| 4,503,569 | 3/1985 | Dotter | 3/1.4 |
| 4,830,003 | 5/1989 | Wolff et al. | 128/343 |
| 4,994,066 | 2/1991 | Voss | 606/108 |
| 5,044,369 | 9/1991 | Sahota | 128/658 |
| 5,192,297 | 3/1993 | Hull | 606/195 |
| 5,201,901 | 4/1993 | Harada et al. | 606/198 |
| 5,224,953 | 7/1993 | Morgentaler | 606/192 |
| 5,344,425 | 9/1994 | Sawyer | 606/198 |
| 5,562,641 | 10/1996 | Flomenblit et al. | 604/281 |
| 5,601,591 | 2/1997 | Edwards et al. | 606/198 |
| 5,607,466 | 3/1997 | Imbert et al. | 623/1 |
| 5,667,522 | 9/1997 | Flomenblit et al. | 606/198 |
| 5,766,237 | 6/1998 | Cragg | 623/1 |

*Primary Examiner*—Michael Buiz
*Assistant Examiner*—Anthony King
*Attorney, Agent, or Firm*—Lyon & Lyon LLP

[57] ABSTRACT

Two embodiments for a stent delivery catheter are disclosed. In the first embodiment, the stent delivery catheter comprises an outer sheath, a peel-away sheath, and an inner sheath. In the second embodiment, the stent delivery catheter comprises an outer sheath and an inner tubular member which distally ends in a tongue having an arcuate cross section.

7 Claims, 10 Drawing Sheets

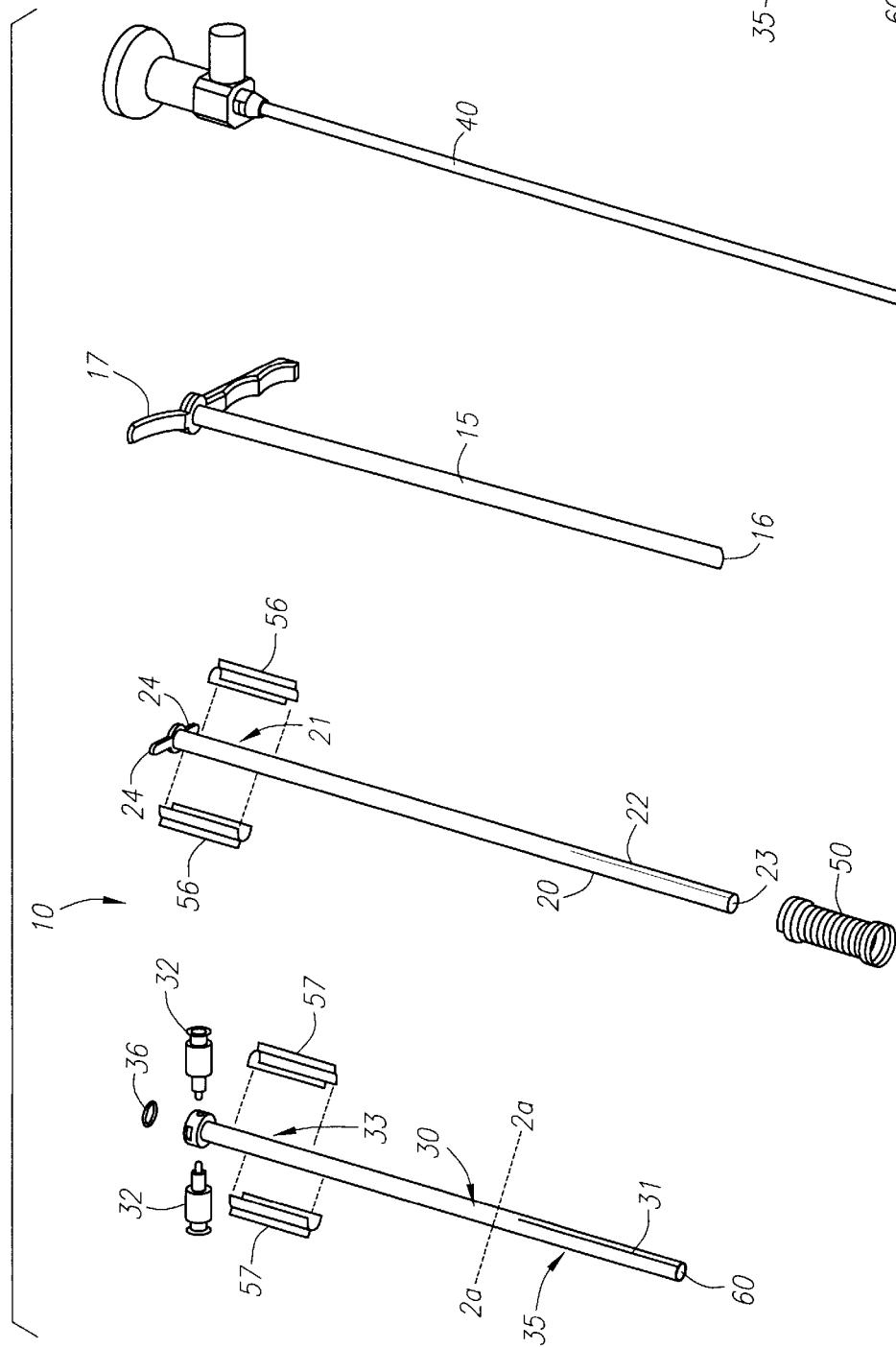
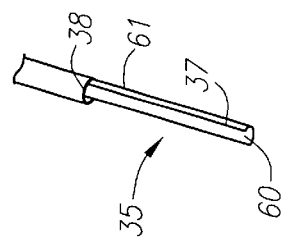

INSERTION DEVICE FOR STENTS AND METHODS FOR USE

INTRODUCTION

This invention relates to stent delivery systems to facilitate the treatment of prostate disease, including benign prostate hypertrophy or prostate cancer.

BACKGROUND OF THE INVENTION

Benign prostate hypertrophy, also known as benign prostate hyperplasia (BPH) commonly afflicts men beginning at age 50. The prostate swells and presses on the urethra, making urination difficult and uncomfortable. In addition, it may cause urination urgency. Also afflicting older men is prostate cancer which may metastasize and cause death. Early treatment can reduce the risks of death from prostate cancer.

Both prostate enlargement and prostate cancer may be treated with heat treatments such as hyperthermia or thermotherapy. As described in co-pending U.S. app. Ser. No. 08/629,650, filed Apr. 9, 1996, a stent may serve the dual purpose of acting as a heat source for the thermotherapy procedures, as well as acting to hold the urethra open after therapy to temporarily prevent blockage due to swelling and prostate tissue sloughing. Additionally, a stent may be implanted temporarily while the patient awaits more aggressive surgery or treatment. Rather than implantation after thermotherapy, a stent may be implanted temporarily after cryosurgery or hypothermia. Finally, a stent may be implanted as a primary treatment.

Given the number of therapies employing urethral stents, there is a need in the art for improved stent delivery systems. Eum, U.S. app. Ser. No. 09/063,118, filed Apr. 20, 1998, and incorporated herein by reference, discloses a stent delivery system comprising a catheter with an anchoring mechanism at its distal end that is placed within the bladder. The stent is displaced proximally on the catheter a predetermined distance from the anchor. This ensures that the stent does not affect the bladder sphincter. Placement of a stent within the bladder sphincter could lead to incontinence and other problems. Because the anchoring mechanism must be placed within the bladder, such a stent delivery system requires a flexible endoscope. Many doctors, however, are equipped only with standard rigid urological endoscopes, which cannot maneuver through the prostatic urethra into the bladder. Thus, there is a need in the art for improved stent delivery systems that can accurately and conveniently implant a stent in the prostatic urethra using conventional rigid urological endoscopes.

SUMMARY OF THE INVENTION

The stent delivery systems described below permit placement of a stent in the urethra. The devices efficiently implant a stent into the prostatic urethra under direct vision. The invention has two main embodiments.

In the first embodiment, the invention comprises a bi-petaled insertion catheter including an outer sheath, a peel-away sheath adapted to cover a stent mounted within the outer sheath, and an inner sheath covering a proximal portion of the stent. Upon inserting the catheter into the prostatic urethra, a clinician will guide the distal end of the catheter under direct vision proximally to the bladder sphincter using an endoscope inserted within the inner sheath. Additionally, the clinician could guide the distal end of the catheter using ultrasonic or x-ray imaging. The outer sheath is then proximally displaced, exposing the distal end of the peel-away sheath. The distal end of the stent expands and separates longitudinal slits within the exposed portion of the peel-away sheath and begins gripping the urethral wall. By distally displacing the inner sheath with respect to the peel-away sheath and the outer sheath, a clinician distally displaces the distal portion of the stent from the peel-away sheath. Thus exposed, the distal portion of the stent grips the prostatic urethra, allowing the clinician to then fully separate the peel away sheath along its longitudinal slits and retract the peel-away sheath and the inner sheath from the stent to complete the stent deployment.

In a preferred second embodiment, the invention comprises a single-petaled catheter including an outer sheath and an inner tubular member. The inner tubular member ends distally in an elongated tongue having an arcuate cross section. The clinician guides the distal end of the catheter into position using an endoscope inserted within the lumen of the inner tubular member and/or using ultrasonic or x-ray imaging. After positioning the catheter, the clinician proximally displaces the outer sheath to expose the tongue of the inner tubular member. The distal end of the stent expands against the now exposed tongue to begin gripping the urethral wall. When satisfied with the final stent position, the clinician proximally withdraws the inner tubular member away from the stent, using the distal end of the outer sheath to prevent proximal displacement of the stent. The outer sheath may then be withdrawn, completing the stent deployment.

DESCRIPTION OF THE DRAWINGS

FIG. 2 is an exploded view of the stent deployment device shown in FIG. 1.

FIG. 2a is a side-elevational view of the stent deployment device shown in FIG. 1 wherein the distal portion of the inner sheath is adapted with a tongue having an arcuate cross section.

DETAILED DESCRIPTION OF THE INVENTION

The stent deployment device according to the present invention has two main embodiments. In the first embodiment, the stent deployment device comprises a bi-petaled catheter. In the second embodiment, the stent deployment device comprises a single-petaled catheter. The bi-petaled catheter will be described first.

The Bi-petaled Catheter Embodiment

Figure 1:
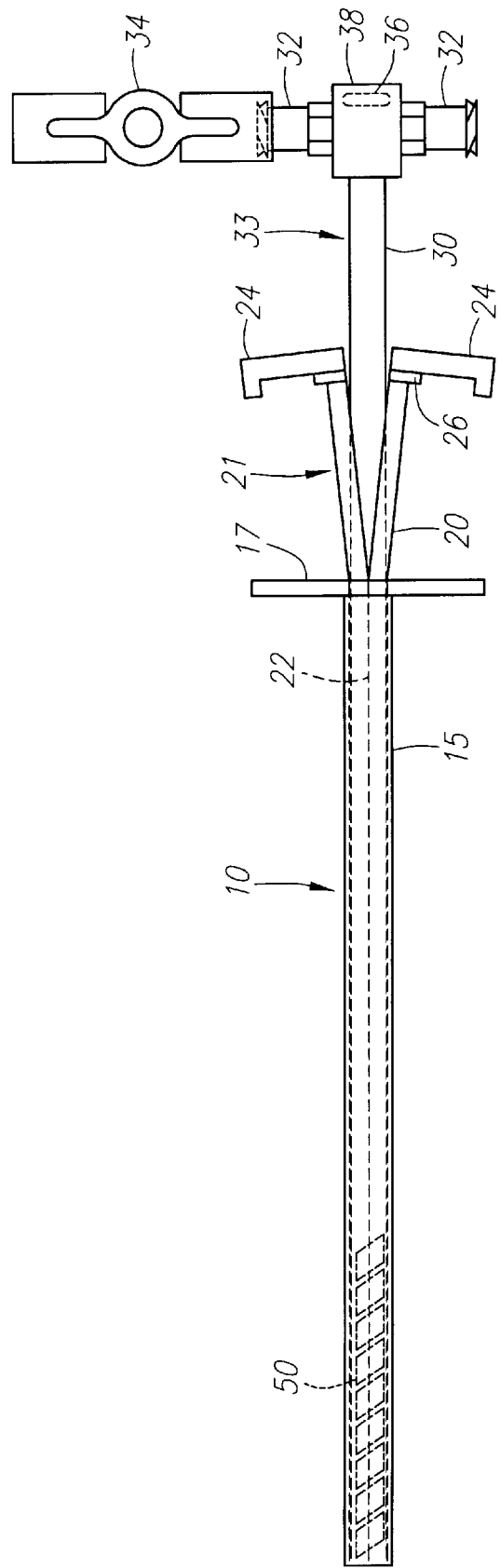
FIG. 1 is a side-elevational view of a bi-petaled embodiment of a stent deployment device in accordance with the present invention.

Turning now to the figures, a bi-petaled catheter 10 is illustrated in FIGS. 1 and 2. A rigid outer sheath 15 with outer sheath handle 17 surrounds a peel-away sheath 20 slidably disposed within the lumen of outer sheath 15. Peel-away sheath 20 has slits 22 extending longitudinally from its distal end 23 towards peel-away handles 24. Handles 24 are preferably joined by an easily-torn tab 26 (shown torn in FIG. 1) positioned at the proximal end of slits 22. Because peel-away sheath 20 is flexible, preferably constructed of Teflon (FEP) material, a clinician can easily pull apart peel-away handles 24 to tear tab 26 in order to retract the peel-away sheath 20 after stent deployment. Prior to deployment, peel-away sheath 20 may completely or substantially cover stent 50 which is disposed within the lumen of peel-away sheath 20 whereby the distal end of stent 50 is substantially aligned with the distal end 23 of peel-away sheath 20.

Inner sheath 30 is preferably constructed of Teflon (FEP) material and is slidably disposed within the lumen of peel-away sheath 20. Inner sheath 30 has a distal portion 35 adapted to receive a proximal portion of stent 50. In one embodiment, illustrated in FIG. 2, the distal portion 35 of inner sheath 30 has longitudinal slits 31 extending proximally from its distal end. Thus, in this embodiment of the bi-petaled catheter 10, distal portion 35 covers the proximal portion of stent 50 in a fashion similar to the manner in which peel-away sheath covers stent 50 as illustrated in FIG. 1.

In a second embodiment of the bi-petaled catheter 10, the distal portion 35 of inner sheath 30, illustrated in FIG. 2a, comprises a tongue 37 having an arcuate cross-section. Tongue 37 has an outer surface 61 adjacent to inner surface of the peel-away sheath 20 and an inner surface 60 facing the lumen of inner sheath 30. The proximal portion of stent 50 is disposed on the inner surface 60 of tongue 37 prior to stent deployment.

Those skilled in the art will appreciate that many other materials for peel-away sheath 20 and inner sheath 30 besides Teflon may be used in accordance with the present invention. Given the flexibility of peel-away sheath 20 and inner sheath 30, outer sheath 15 preferably is suitably rigid to protect the often-fragile endoscopes that may be used during stent deployment. Thus, outer sheath 15 is preferably constructed of surgical steel to provide the proper rigidity without possessing too large a diameter. This allows for easy insertion into the urethra.

Inner sheath 30, in order to facilitate endoscopic vision, preferably is constructed of a transparent form of Teflon or other suitable material. Luer ports 32 attached to the proximal end of inner sheath 30 allow the introduction of saline or other fluids into the urethra during stent deployment. Luer ports 32 may be fitted with valves 34 (shown in FIG. 1). A seal 36 prevents fluid from leaking when an endoscope 40 is inserted through the adapter port 38 into the lumen of inner sheath 30.

The endoscope 40 shown in FIG. 2 may be one of many conventional models of endoscopes. The endoscope 40, whether provided with the system or provided separately, also forms a part of the deployment system. The term endoscope is used in this specification to denote any scope that may be used with the delivery system, although scopes of various designs are referred to by different names such as laparoscopes and cystoscopes. The invention preferably is designed to accommodate conventional rigid endoscopes because such scopes are more commonly distributed in doctors' offices than flexible endoscopes. However, the stent delivery system of the present invention may be used with either rigid or flexible endoscopes.

Prior to deployment, stent 50 is coiled within the lumen of distal end 23 of peel-away sheath 20. The proximal portion of stent 50 is also coiled within the lumen of distal portion 35 of inner sheath should the distal portion 35 be adapted with longitudinal slits 31. If the distal portion 35 is adapted with tongue 37, the coiled proximal portion of stent 50 is instead disposed on the inner surface 60 of tongue 37. Stent 50 preferably is constructed out of a shape memory alloy such as Nitinol in a helical shape. Prior to placement within the catheter 10, stent 50 is in its pliable martensitic state. The austenitic transition of stent 50 preferably occurs at body temperature whereby heated saline is not required to activate the stent. Alternatively, the austenitic transition of stent 50 may be slightly higher than body temperature whereby heated saline introduced through the luer ports 32 of inner sheath 30 could be used to transition stent 50 from the martensitic to the austenitic state.

As illustrated in FIG. 1, prior to deployment, the distal end 23 of peel-away sheath 20 substantially aligns with the distal end 16 of outer sheath 15. Because peel-away sheath 20 is longer than outer sheath 15, it thus extends proximally from outer sheath handle 17. Outer sheath 15 may be displaced proximally along this proximal extension 21 of peel-away sheath 20. To prevent a premature proximal displacement of outer sheath 15 when catheter 10 is inserted into the urethra, a restrainer 56 may clamp along the proximal extension 21 of peel-away sheath 20. Preferably, at least one restrainer 56 having an arcuate cross section adapted to clamp around peel-away sheath 20 is placed along the proximal extension 21 of peel-away sheath 20 prior to stent deployment as illustrated in FIG. 2.

Similarly, as illustrated in FIG. 1, inner sheath 30 extends proximally from the peel-away sheath pull handles 24. Thus, peel-away sheath 20 may be displaced proximally along the proximal extension 33 of inner sheath 30. Alternatively, inner sheath 30 could be displaced distally with respect to peel-away sheath 20. To prevent a premature displacement of peel-away sheath 20 with respect to inner sheath 30 when catheter 10 is inserted into the urethra, preferably at least one restrainer 57 having an arcuate cross section adapted to clamp around inner sheath 30 is placed along the proximal extension 33 of inner sheath 30 prior to insertion as illustrated in FIG. 2. Those of ordinary skill in the art will appreciate that many other suitable configurations exist for restrainers 56 and 57.

Figure 3:
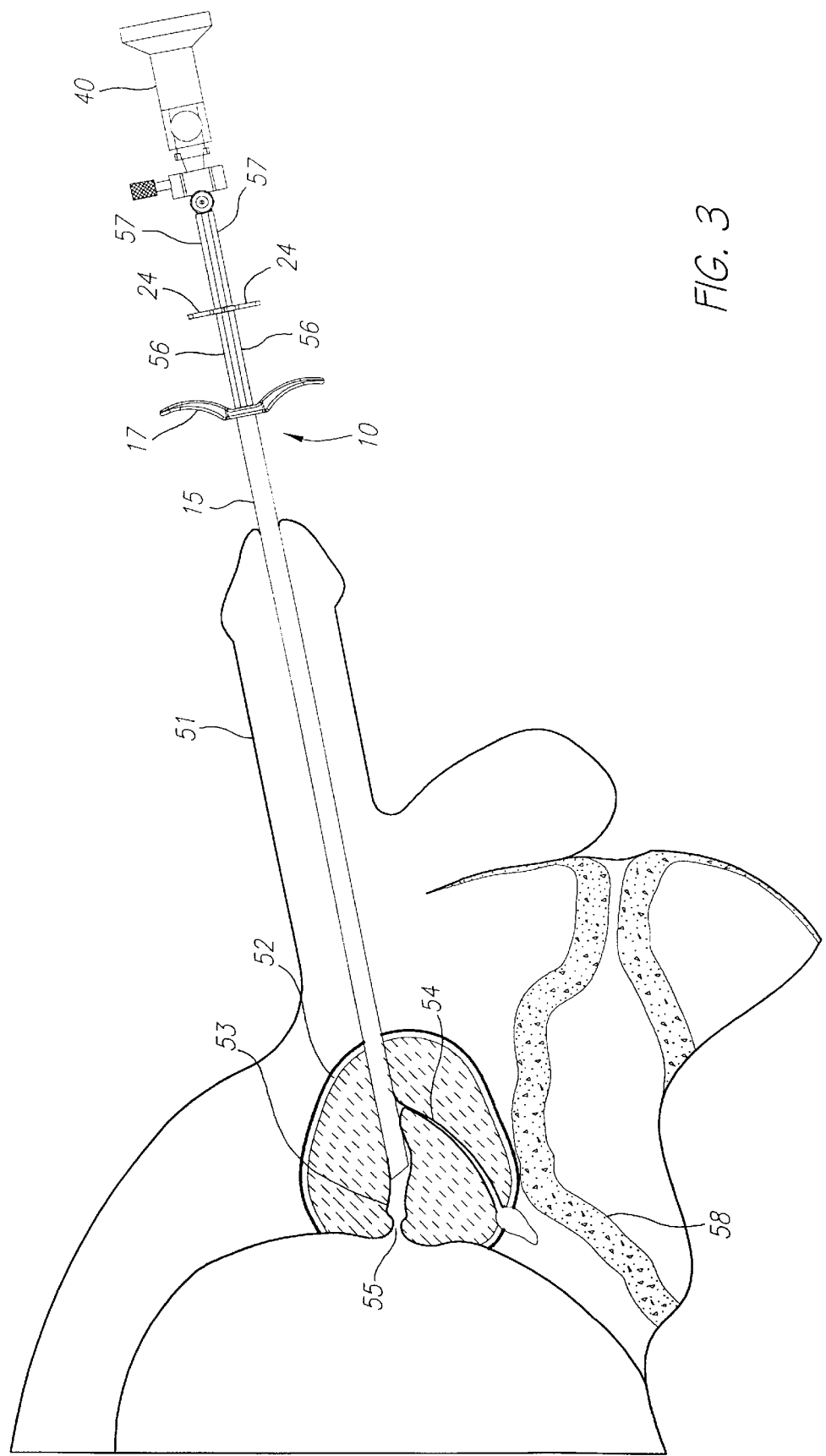
FIG. 3 is a cross sectional view of the stent deployment device of FIG. 1 in position to begin stent deployment.

FIGS. 3 through 6 illustrate a method of stent deployment using the bi-petaled catheter embodiment. FIG. 3 illustrates the insertion of a catheter 10 via the penis 51 into the prostatic urethra 53. Prostatic urethra 53 ends distally at bladder sphincter 55 and is surrounded by the prostate 52. Using endoscope 40, the clinician determines that the distal end of the outer sheath 15 is proximal to the bladder sphincter 55 and distal to the seminal vesicles 54. Saline or other suitable fluid pumped down the inner sheath through luer ports 32 assists the endoscopic imaging of the distal end of outer sheath 15. In addition, the clinician may verify the location of catheter 10 with respect to prostatic urethra 53 by using ultrasonic imaging. Ultrasonic imaging would require, for example, an ultrasound transducer to be placed in the rectum 58. Instead of ultrasonic imaging or in addition thereto, the clinician could employ x-ray imaging to verify the location of catheter 10 within prostatic urethra 53.

Figure 4:
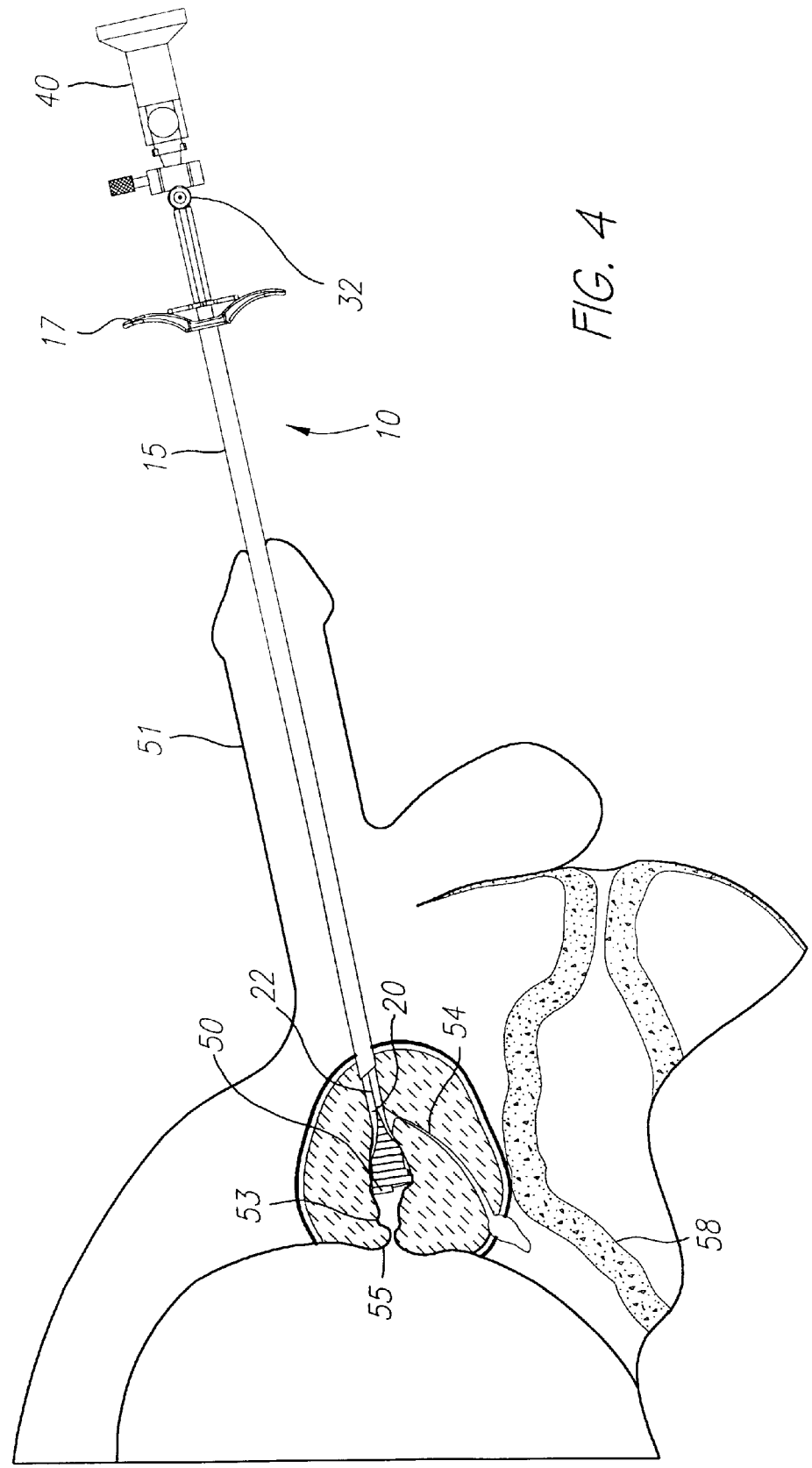
FIG. 4 is a cross sectional view of the stent deployment device of FIG. 1 in initial deployment.

Satisfied that the catheter 10 has been properly placed within prostatic urethra 53, the clinician may begin the initial deployment of stent 50. As illustrated in FIG. 1, the distal end of stent 50 is substantially aligned with the distal end 23 of peel-away sheath 20 which in turn is substantially aligned with the distal end 60 of outer sheath 15. Thus a proximal displacement of outer sheath 15 with respect to peel-away sheath 20 preferably will immediately uncover the distal portion of peel-away sheath 20. Before performing this displacement, the clinician removes restrainers 56 from the proximal extension of peel-away sheath 20. The clinician then displaces the outer sheath 15 proximally as illustrated in FIG. 4. This exposes the distal end 23 of peel-away sheath 20. Stent 50, having reached its austenitic state either by sensing body temperature or through exposure to warm saline pumped down luer ports 32, can now expand within the flexible peel-away sheath. Because outer sheath 15 is rigid, stent 50 can only so expand within the now-exposed portion of peel-away sheath 20.

The expansion of stent 50 forces the exposed portion of peel-away sheath 20 to separate along its longitudinal slits 22. As stent 50 separates peel-away sheath 20 along the two longitudinal slits 22, the distal end 23 of peel-away sheath 20 resembles two flower petals. Hence, this embodiment of the invention is denoted a bi-petaled catheter. Peel-away sheath 20 preferably has two longitudinal slits 22. Thus, when pull handles 24 are separated (tearing tab 26), peel-away sheath 20 separates longitudinally into halves. However, those of ordinary skill in the art will realize that a plurality of longitudinal slits 22 greater than two could be used. Such a plurality of longitudinal slits 22 would require a corresponding plurality of pull handles 24.

Although stent 50 abuts the urethral wall through longitudinal slits 22, it is still largely covered by peel-away sheath 20. Because peel-away sheath 20 has a smooth surface, stent 50 may still be re-positioned within the prostatic urethra 53 during this stage of its deployment. This allows a clinician to check the location of stent 50 using an endoscope 40 before moving to the secondary deployment stage.

Figure 5:
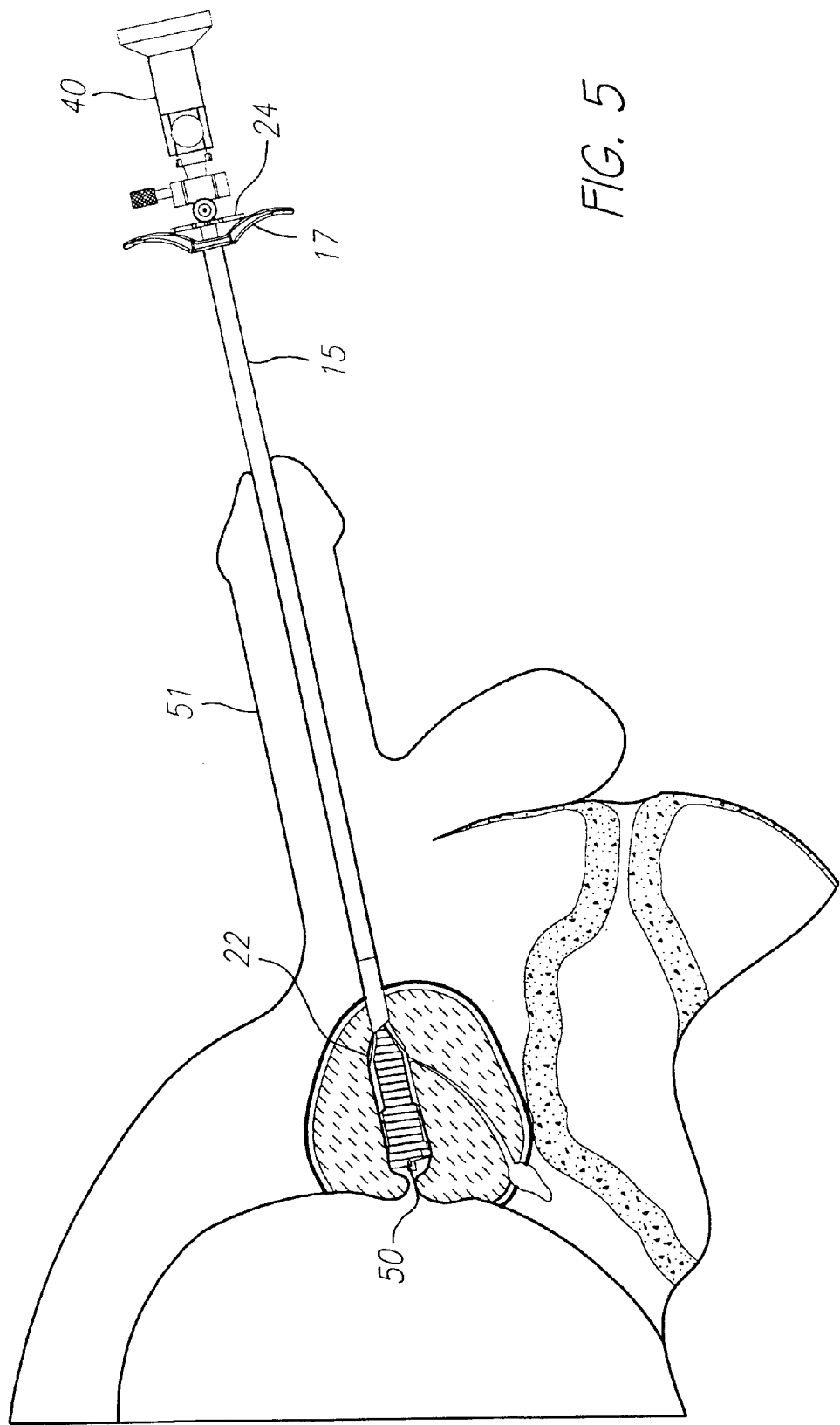
FIG. 5 is a cross sectional view of the stent deployment device of FIG. 1 in secondary deployment.

The secondary deployment stage is illustrated in FIG. 5. After re-checking the position of stent 50 and adjusting as necessary, the clinician removes restrainers 57 from the proximal extension of inner sheath 30. The clinician then distally displaces inner sheath 30 with respect to peel-away sheath 20. As illustrated in FIG. 1, prior to this displacement, the distal end 60 of inner sheath 30 was proximally displaced from the distal end 23 of peel-away sheath 20. After the distal displacement of inner sheath 30, the distal ends of inner sheath 30 and peel-away sheath 20 are substantially aligned. In turn, this distally displaces the distal portion of stent 50 from peel-away sheath 20. Regardless of whether distal portion 35 of inner sheath 30 exists in the longitudinal slit 31 embodiment or in the tongue 37 embodiment, stent 50 cannot displace proximally past distal portion 35 in the lumen of inner sheath 30. Thus, the distal displacement of inner sheath 30 with respect to peel-away sheath 20 forces the distal portion of stent 50 distally away from the distal end of peel-away sheath 20. Therefore, a clinician generally will place stent 50 slightly proximal to the desired final location before performing this secondary deployment. The clinician may gauge the distal displacement by the length of restrainers 57. The desired location prior to secondary deployment of the stent would be proximally displaced the length of restrainers 57. After secondary deployment, stent 50 is now fully uncovered at its distal end. This uncovered distal end prevents further movement of stent 50 through frictional engagement of the prostatic urethra 53. The clinician may now fully deploy stent 50.

As previously described, distal portion 35 of inner sheath 30 in the bi-petaled catheter 10 may exist in either the longitudinal slit 31 embodiment or in tongue embodiment 35. Each embodiment has its advantages. For example, in the longitudinal slit 31 embodiment, the proximal portion of stent 50 is completely covered and gripped by distal portion 35 of inner sheath 30. This assists the distal displacement of stent 50 with respect to peel-away sheath 20. However, stent 50 may tangle with the distal portion 35 because of meshing with the longitudinal slits 31. This tangling is avoided by the tongue 37 embodiment, which of course does not possess longitudinal slits 31. Nevertheless, because tongue 37 does not completely cover and grip the proximal portion of stent 50, it may kink stent 50 with respect to tongue 37 as distal portion 35 distally displaces stent 50 with respect to peel-away sheath 20. This kinking is alleviated by a radially extending projection or bump 38 at the proximal base of tongue 37 which assists distally displacing stent 50 in a direction parallel to the lumen of inner sheath 30.

Figure 6:
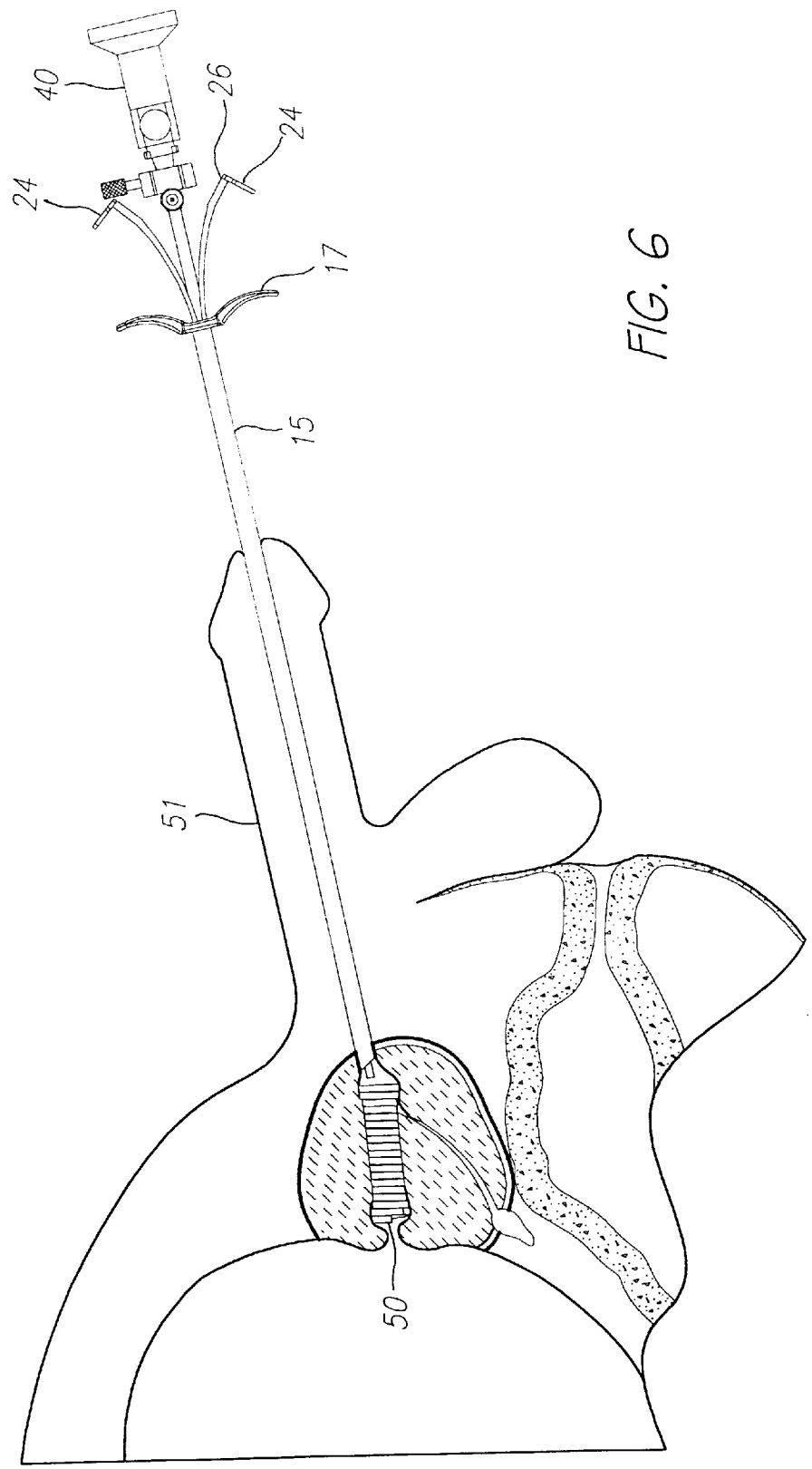
FIG. 6 is a cross sectional view the stent deployment device of FIG. 1 in full deployment.

Full deployment of stent 50 is illustrated in FIG. 6. The clinician separates pull handles 24, tearing apart tab 26. The separated halves of peel-away sheath, having been "peeled-away" from one another, may now be completely retracted from stent 50. Stent 50 does not proximally displace with this retraction because the already-deployed distal end of stent 50 anchors it in the prostatic urethra 53. Similarly, inner sheath 30 may also be proximally retracted from stent 50 without any displacement of stent 50. Stent 50, freed from the peel-away sheath 20 and outer sheath 15, may now expand completely and lodge against the prostatic urethral wall 53. After a final check on the position of stent 50 through endoscope 40, the clinician may retract catheter 10 from the penis 51, completing the stent deployment.

The Single-petaled Catheter Embodiment

Figure 7:
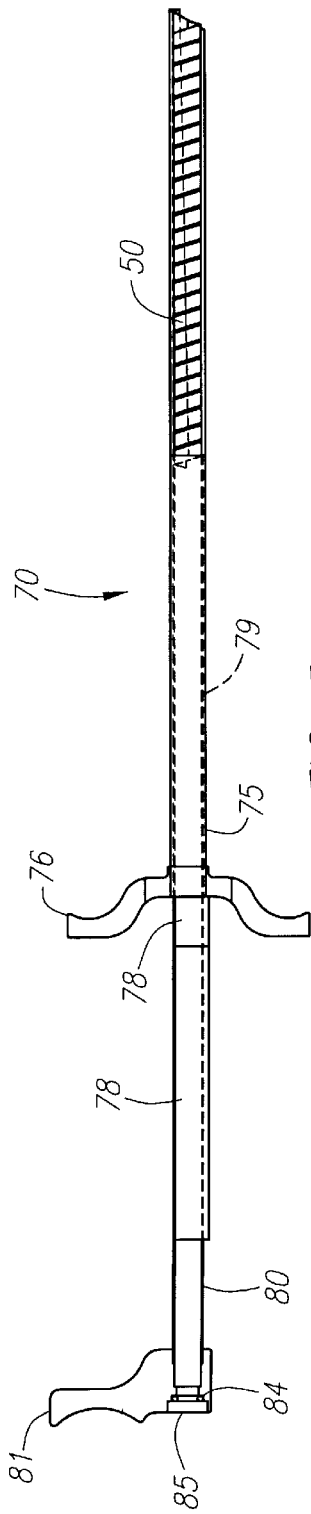
FIG. 7 is a side elevational view, partially cut-away, of a single-petaled embodiment of a stent deployment device in accordance with the present invention.
Figure 8:
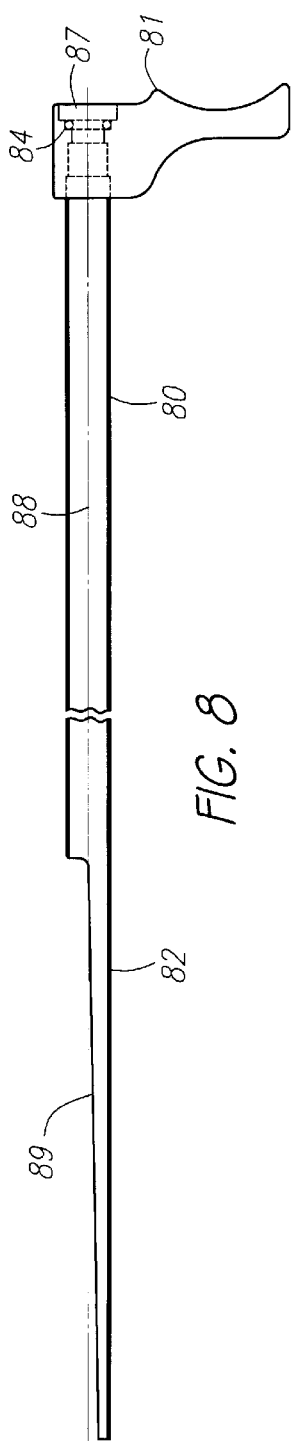
FIG. 8 is a side elevational view of the inner tubular member of the stent deployment device shown in FIG. 7.
Figure 9:
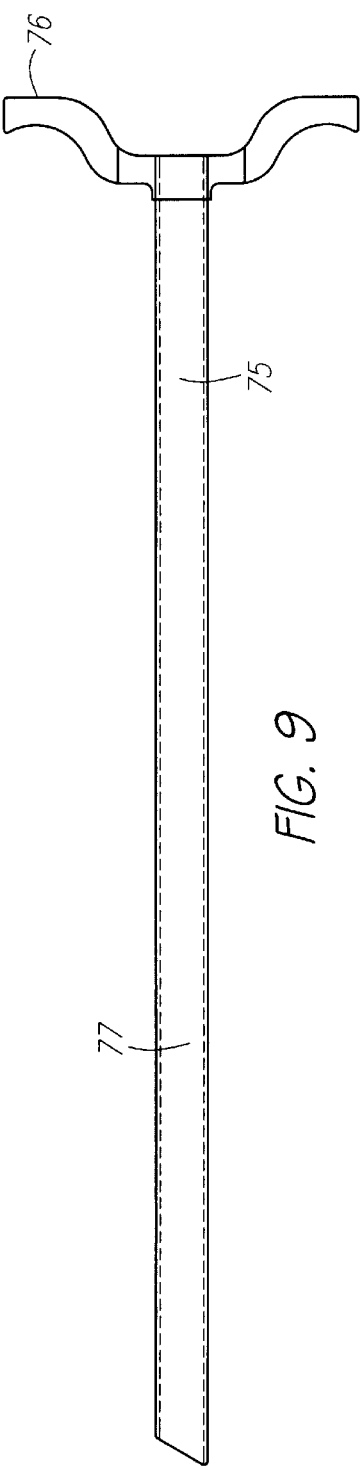
FIG. 9 is a side elevational view of the outer sheath of the stent deployment device shown in FIG. 7.

Turning now to FIGS. 7–10, the single-petaled catheter, which is the preferred embodiment, is illustrated. FIG. 7 illustrates a cross sectional view of single-petaled catheter 70 including an outer sheath 75 and an inner tubular member 80 slidably disposed within the lumen of outer sheath 75. Inner tubular member 80 has an adapter port 85 for the introduction of a conventional endoscope 40 (illustrated in FIGS. 11 through 14) into the lumen 88 of inner tubular member 80. Saline or other suitable fluids may be pumped into the lumen 88 of inner tubular member 80 through luer ports 83. Seal 84 prevents leakage of fluid from adapter port 85.

The distal end of inner tubular member 80 is formed into an elongated tongue 82 having an arcuate cross section. Thus, because the tongue 82 resembles a single flower petal, this embodiment is denoted a single-petaled catheter 70 as compared to the bi-petaled catheter 10. Unlike the bi-petaled catheter 10, in which the peel-away sheath 20 must be flexible to permit expansion of stent 50 as outer sheath 15 is proximally displaced during deployment, inner tubular member 80 and tongue 82 may be constructed out of a rigid material, preferably medical grade polycarbonate or similar plastic. Because tongue 82 and inner tubular member 80 are rigid, outer sheath 80 may be constructed of polycarbonate plastic also. This contrasts with the bi-petaled catheter 10 in which outer sheath 15 is preferably made of surgical stainless steel. Outer sheath 15 preferably has suitable rigidity to protect often-fragile endoscopes during insertion of catheter 10 into the urethra because peel-away sheath 20 and inner sheath 30 are flexible. Outer sheath 80 in single-petaled catheter 70 need not provide the same degree of rigidity because inner tubular member 80 is far more rigid, helping to protect endoscope 40 during insertion. Manufacturing outer sheath 80 from polycarbonate plastic rather than steel is not only cheaper but also offers less friction to movements of stent 50. A steel outer sheath would grip stent 50 more firmly, thus hampering stent deployment, because of the greater friction which would exist between the steel outer sheath and stent 50.

Elongated tongue 82 preferably has an arcuate cross section, more preferably approaching 180° in arc. Thus, in this preferred embodiment, tongue 82 is a longitudinally divided half of tubular member 80. However, the width and arc of tongue 82 may range widely without departing from the spirit of this invention. Indeed, tongue 82 could approach a flattened columnar shape. Those of ordinary skill in the art will appreciate the range of shapes tongue 82 could have while still maintaining its function. The longitudinal length of tongue 82 should extend substantially along the length of stent 50, more preferably along the full length of stent 50 as illustrated in FIGS. 7 and 10.

Figure 10:
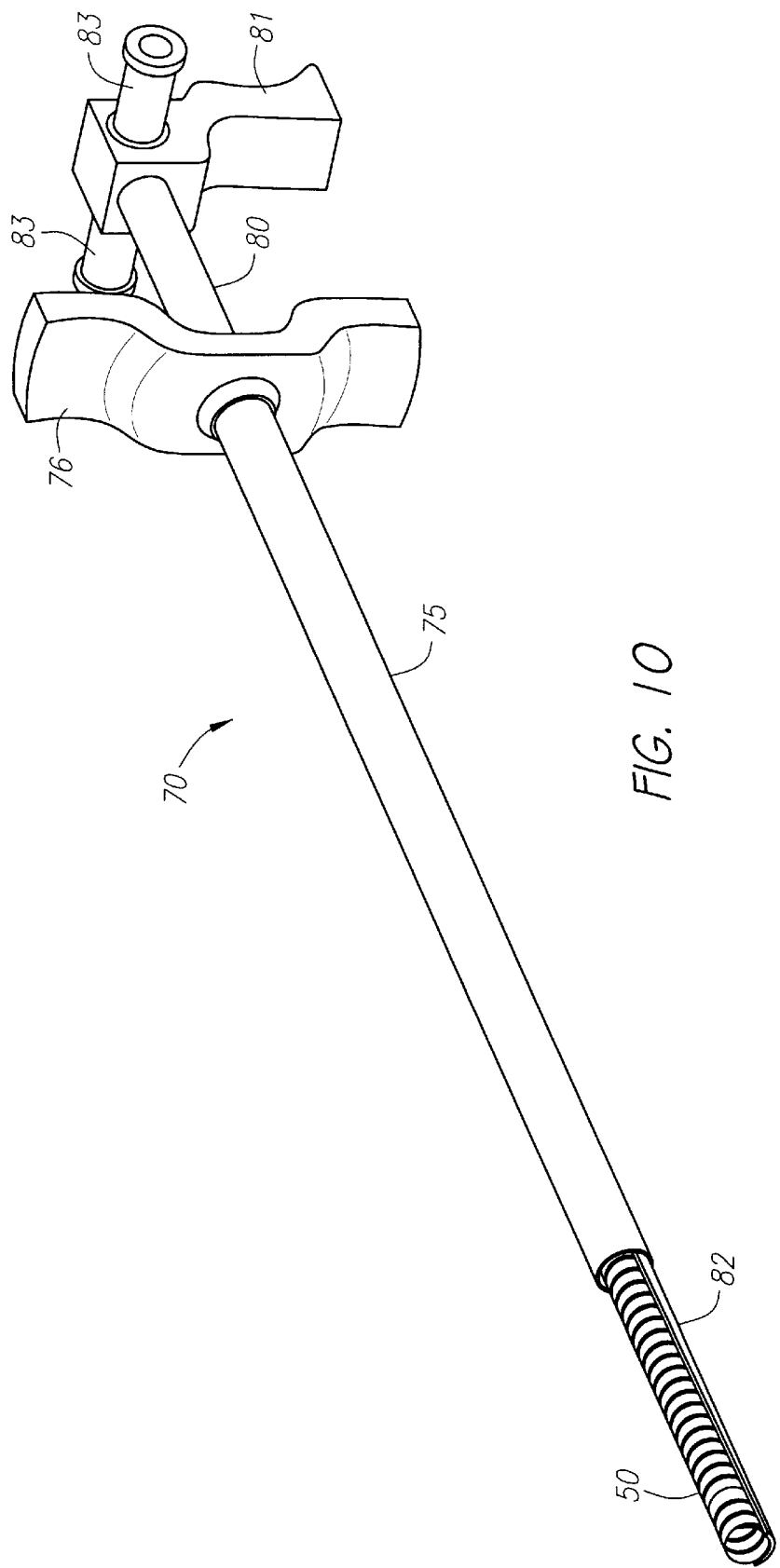
FIG. 10 is side elevational view of the stent deployment device shown in FIG. 7 with the outer sheath proximally displaced to expose the elongated tongue of the inner tubular member and the stent.

Prior to deployment, helical-shaped stent 50 lies coiled between the inner surface 89 of tongue 82 and the inner lumen wall 79 of outer sheath 75 as illustrated in FIG. 7 and 10. Thus, tongue 82 receives and supports stent 50 within the lumen of outer sheath 75 but does not envelop stent 50 as did peel-away sheath 20 in the bi-petaled embodiment. In addition, the lumen of inner tubular member 80 is sized such that stent 50 cannot displace proximally past tongue 82 into the lumen of inner tubular member 80. Tongue 82 greatly reduces the friction between stent 50 the outer sheath 75, thereby assisting the stent deployment process.

Before deployment, stent 50 is in the martensitic or compressed stage. In FIG. 10, outer sheath 75 is displaced proximally with respect to stent 50 and tongue 82. In the urethra, this would expose the stent 50 to body heat, causing the stent 50 to transition to an austenitic or expanded state. Alternatively, warm saline pumped down luer ports 83 could assure that stent 50 transitions into the austenitic stage. Unlike the stent 50 in bi-petaled catheter 10, stent 50 in the single-petaled catheter 70 has substantial contact with the inner lumen wall 79 of outer sheath 75. This is not a problem, however, because the polycarbonate material of outer sheath 75 offers little resistance to movements of stent 50.

As similarly used on the bi-petaled catheter 10, restrainers 77 and 78 are placed on single-petaled catheter 70 to prevent premature displacements of outer sheath 75 during insertion of the catheter 70 into the penis 51 and prostatic urethra 53. As illustrated in FIG. 7, tubular member 80 has a greater length than outer sheath 75. Thus, when tubular member 80 is inserted into outer sheath 75 so that the distal end of tongue 82 is substantially aligned with the distal end of outer sheath 75, tubular member 80 will have a proximal extension extending proximally from handle 76 of outer sheath 75. Outer sheath 75 could be displaced proximally on this proximal extension of tubular member 80. Restrainers, which clamp about the surface of this proximal extension of tubular member 80 prevent any premature proximal displacement during insertion of catheter 70 into the urethra. In the preferred embodiment, restrainers 78 and 77 clamp about the proximal extension of tubular member 80. Restrainers 78 have an appropriately shaped arcuate cross section to facilitate clamping about tubular member 80. Those of ordinary skill will appreciate the widely varying shapes restrainers 78 and 77 could have while still retaining their clamping function.

Figure 11:
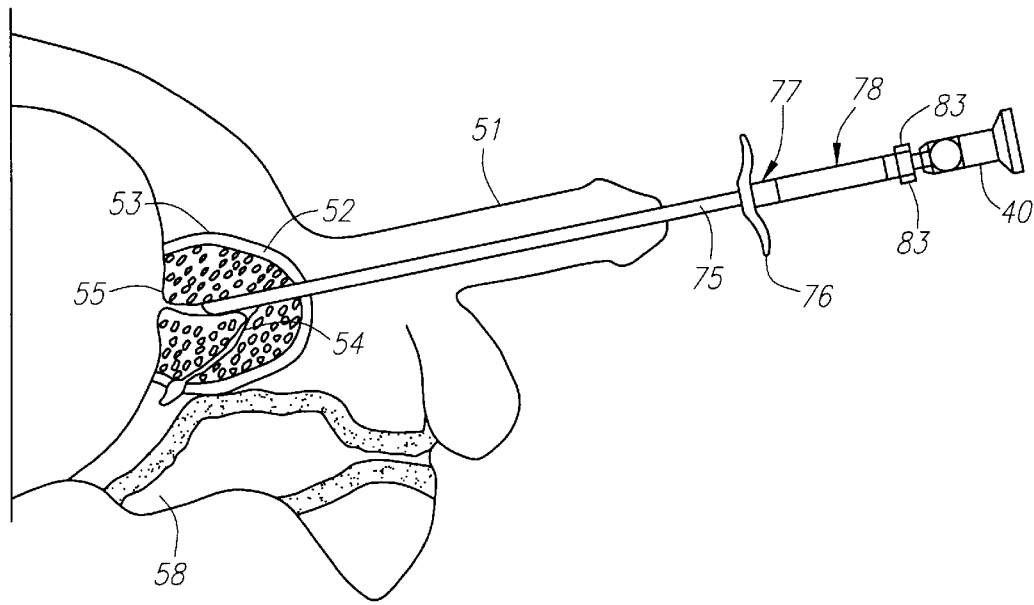
FIG. 11 is a cross sectional view of the stent deployment device of FIG. 1 in position to begin stent deployment.

FIGS. 11 through 14 illustrate the stent deployment method using the single-petaled catheter embodiment. FIG. 11 illustrates the insertion of the catheter 70 through the penis 51 into the prostatic urethra 53. Using endoscope 40, the clinician determines that the distal end of the outer sheath 75 is proximal to the bladder sphincter 55 and distal to the seminal vesicles 54. Saline or other suitable fluid pumped down the lumen of tubular member 80 through luer ports 32 assists the endoscopic imaging of the distal end of outer sheath 75. In addition, the clinician may verify the location of catheter 70 with respect to prostatic urethra 53 by using ultrasonic imaging. Such imaging would require, for example, an ultrasound transducer to be placed in the rectum 58. Instead of ultrasonic imaging or in addition thereto, the clinician could employ roentgenographic imaging to verify the location of catheter 10 within prostatic urethra 53. Satisfied that the catheter 70 has been properly placed within prostatic urethra 50, the clinician may begin initial deployment of stent 50.

Figure 12:
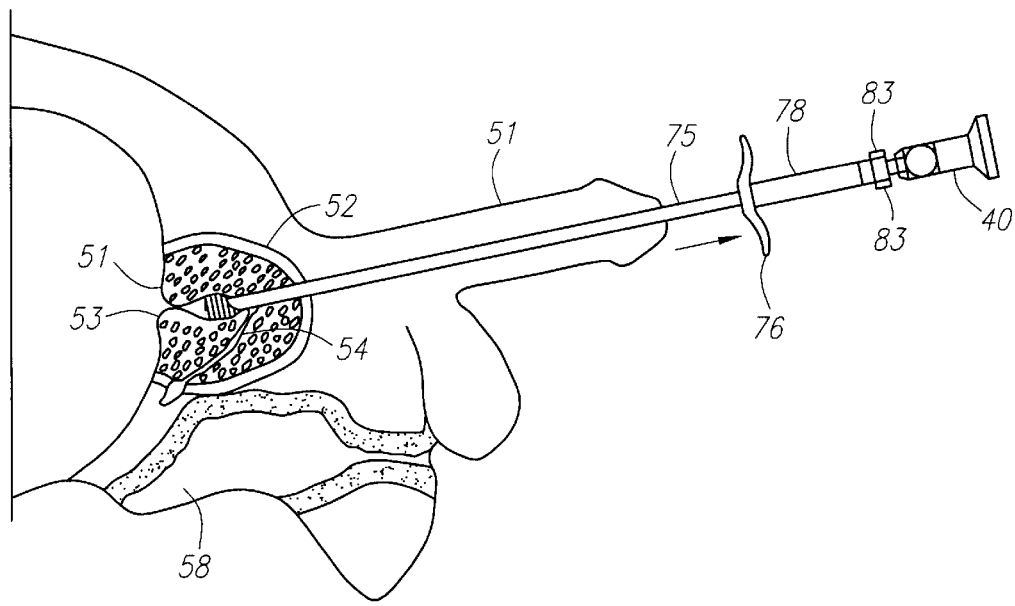
FIG. 12 is a cross sectional view of the stent deployment device of FIG. 1 in the initial deployment stage.

Initial deployment of stent 50 by single-petaled catheter 70 is illustrated in FIG. 12. Restrainers 77 that had been placed about the proximal extension of tubular member 20 are removed. The clinician then displaces outer sheath 75 proximally as shown in FIG. 12. Restrainers 77 are sized so that the proximal displacement of outer sheath 75 exposes only a few coils at the distal end of helically shaped stent 50. Having reached its austenitic state either by sensing body temperature or through exposure to warm saline pumped into luer ports 83, these coils of stent 50 expand and begin gripping prostatic urethra 53. But because only a few coils are so deployed, the clinician may check their position and coil spacing using endoscope 40 fluid and adjust if necessary before starting secondary deployment.

Figure 13:
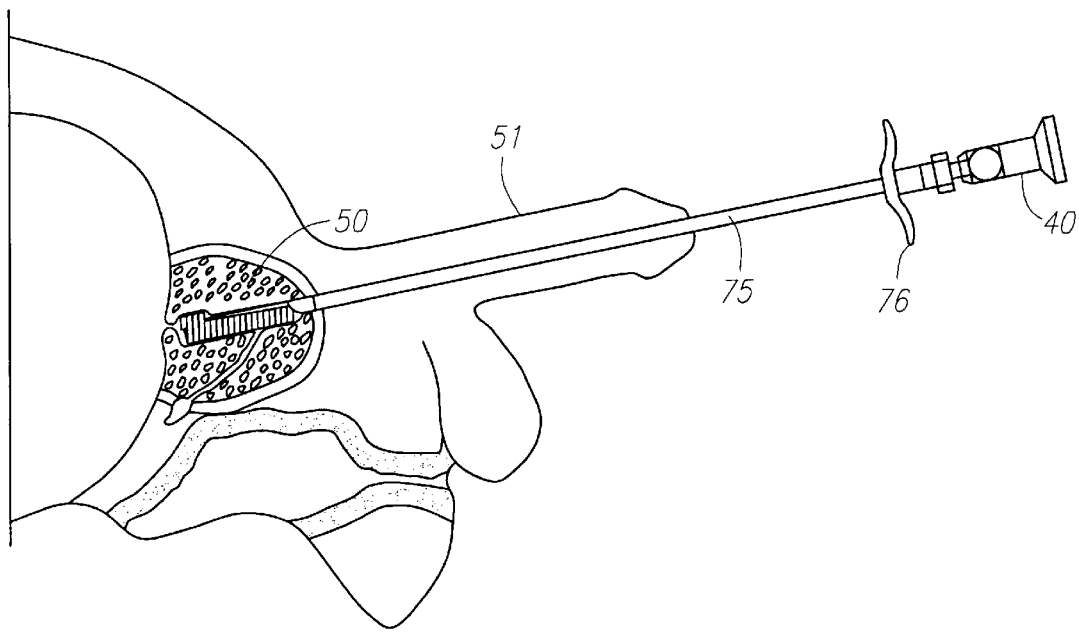
FIG. 13 is a cross sectional view of the stent deployment device of FIG. 1 in the secondary deployment stage.

Secondary deployment of stent 50 using single-petaled catheter 70 is illustrated in FIG. 13. Satisfied that the distal end of stent 50 is in proper position proximal to bladder sphincter 55 in prostatic urethra 53, the clinician removes restrainers 78. This allows a further proximal displacement of outer sheath 75 with respect to tubular member 80 whereby tongue 82 is exposed. In turn, stent 50, having reached its austenitic state, expands along the length of tongue 82 to grip prostatic urethra 53. This allows the clinician to proceed to full deployment.

Figure 14:
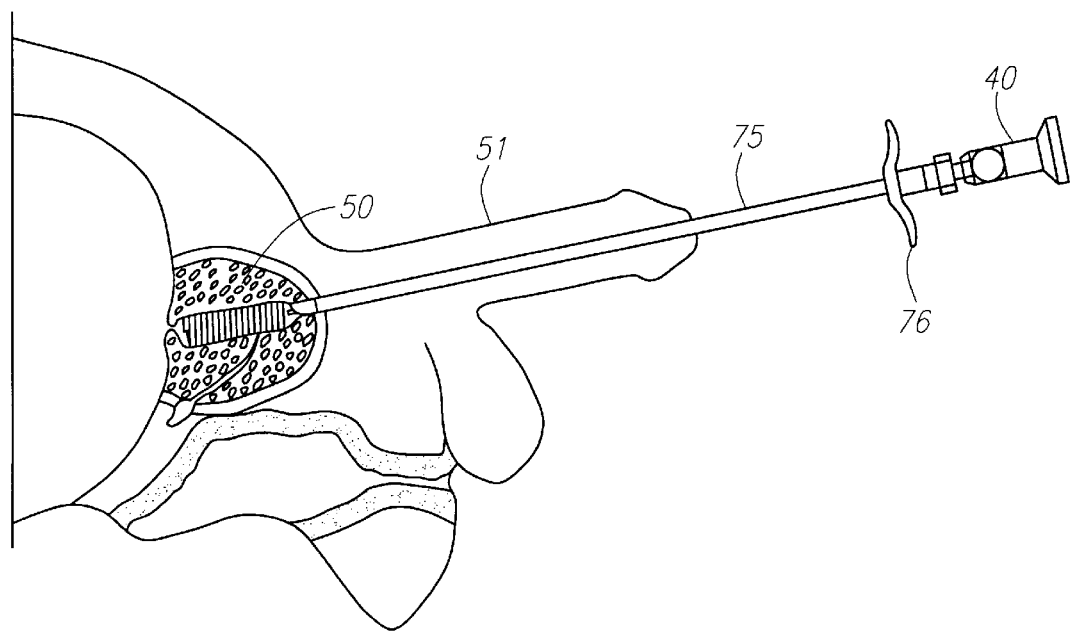
FIG. 14 is a cross sectional view of the stent deployment device of FIG. 1 in the full deployment stage.

Full deployment is illustrated in FIG. 14. The proximal end of stent 50 abuts against the distal end of outer sheath 75. Thus, tubular member 80 may be proximally retracted with respect to outer sheath 75 without displacing stent 50 because the distal end of outer sheath prevents any proximal displacement of stent 50. This stands in contrast to bi-petaled catheter 10 wherein the clinician must distally displace stent 50 during deployment. The only displacement of stent 50 during deployment using single-petaled catheter 70 occurs during the initial deployment stage illustrated in FIG. 12 wherein only a few coils at the distal end of stent 50 contact and grip the prostatic urethra 53. After the clinician is satisfied with stent 50 location during initial deployment, stent 50 is neither proximally nor distally displaced during the remainder of stent deployment, assuring the clinician of proper stent location. Clinicians must be careful in locating the stent in the prostatic urethra 53 because if stent 50 occludes bladder sphincter 55, the patient could be incontinent.

After proximally retracting tubular member 80 from stent 50 as illustrated in FIG. 14, stent 50 is completely deployed in prostatic urethra 53. The clinician may now withdraw single-petaled catheter 70 from penis 51 to complete stent deployment.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

We claim:

1. A stent delivery catheter comprising:

an outer sheath having a distal and proximal end and a lumen therethrough;

a tubular member having a distal and a proximal end and a lumen therethrough, said tubular member slidably disposed in the lumen of said outer sheath, said tubular member ending distally in an elongated tongue having an arc-shaped cross section, said elongated tongue being adapted to receive substantially the full length of a stent; and a stent having a distal and proximal end, said stent disposed along said elongated tongue within the lumen of said outer sheath, wherein the distal end of said stent, the distal end of said elongated tongue, and the distal end of said outer sheath are substantially aligned, and wherein said tubular member has a proximal extension extending proximally from the proximal end of said outer sheath.

2. The stent delivery catheter of claim 1 further comprising:

an adapter port at the proximal end of the outer sheath for receiving an endoscope.

3. The stent delivery catheter of claim 2 further comprising:

a restrainer clamped about the proximal extension of said tubular member whereby proximal displacements of said outer sheath with respect to said tubular member are prevented.

4. The stent delivery catheter of claim 3 wherein said restrainer comprises a first restrainer disposed end-to-end and parallel with a second restrainer.

5. A method of placing a stent within a prostatic urethra, comprising the steps of:

providing a stent delivery catheter comprising:

an outer sheath having a distal and a proximal end and a lumen therethrough;

a tubular member having a distal and a proximal end and a lumen therethrough, said tubular member slidably disposed in the lumen of said outer sheath, said tubular member having an adapter port at its proximal end for receiving an endoscope, said tubular member ending distally in an elongated tongue having an arcuate cross section, said elongated tongue being adapted to receive substantially the full length of a stent;

a stent having a distal end, said stent disposed along said elongated tongue within the lumen of said outer sheath, wherein the distal end of said stent, the distal end of said elongated tongue, and the distal end of said outer sheath are substantially aligned, and wherein said tubular member has a proximal extension extending proximally from the proximal end of said outer sheath;

inserting the catheter through the urethra into the prostatic urethra;

proximally displacing the outer sheath a first distance with respect to the tubular member to the extent whereby a distal portion of the stent is deployed in the prostatic urethra but does not resist further displacement;

proximally displacing the outer sheath with respect to the tubular member a second distance to fully expose the tongue whereby the stent contacts the prostatic urethra substantially along the full length of the stent;

proximally retracting the tongue and tubular member from the stent while steadying the outer sheath to prevent proximal displacement of the stent whereby the stent is fully deployed in the urethra.

6. The method of claim 5 wherein said stent delivery catheter further comprises a first restrainer disposed end-to-end and parallel with a second restrainer, said first and second restrainers clamped about the proximal extension of said tubular member whereby proximal displacements of said outer sheath with respect to said tubular member are prevented, and wherein said method further comprises the steps of:

removing the first restrainer prior to proximally displacing the outer sheath the first distance; and removing the second restrainer prior to proximally displacing the outer sheath the second distance.

7. The method of claim 5 wherein said stent delivery catheter includes an endoscope inserted in the lumen of said tubular member, said method further comprising:

observing the position of said stent using said endoscope during said inserting step and during said proximal displacement steps.

\* \* \* \* \*